United States Patent [19]
Rigoli

[11] 3,952,541
[45] Apr. 27, 1976

[54] APPARATUS FOR QUICK FREEZING OF AQUEOUS SOLUTIONS OR SUSPENSIONS TO BE SUBMITTED TO LYOPHILIZATION

[76] Inventor: Mario Rigoli, Via Falloppio, 5, Milan, Italy

[22] Filed: Dec. 20, 1974

[21] Appl. No.: 534,775

Related U.S. Application Data

[63] Continuation of Ser. No. 194,070, Oct. 29, 1971, abandoned, which is a continuation of Ser. No. 872,679, Oct. 30, 1969, abandoned.

[30] Foreign Application Priority Data

Nov. 5, 1968 Italy .......................... 133846/68[U]
Oct. 16, 1969 Italy ................................. 23480/69

[52] U.S. Cl. .......................................... 62/381; 34/5
[51] Int. Cl.² ............................................ F26B 5/06
[58] Field of Search ....................... 34/5; 62/63, 381

[56] References Cited
UNITED STATES PATENTS

| | | | |
|---|---|---|---|
| 1,928,173 | 9/1933 | Gerstenberg | 62/381 X |
| 2,373,806 | 4/1945 | Barnes | 62/381 X |
| 2,803,888 | 8/1957 | Cerletti | 34/5 X |
| 3,199,216 | 8/1965 | Broadwin | 34/5 X |
| 3,241,250 | 3/1966 | Broadwin | 34/5 X |
| 3,270,434 | 9/1966 | Hackenberg et al. | 34/5 X |

Primary Examiner—William E. Wayner
Attorney, Agent, or Firm—Stevens, Davis, Miller & Mosher

[57] ABSTRACT

Apparatus for quick freezing aqueous solutions or suspensions to be submitted to lyophilization by means of which also the lyophilization time is strongly reduced, characterized in that it comprises:

a. a tiltably hinged tank with refrigerated bottom and walls, the top being shut by a removable air-tight cover;

b. one or more plates or rotating frames for carrying materials to be frozen, rotated at an adjustable speed by means of one or more driven shafts passing through the bottom of the tank.

The rotating plate/s may be refrigerated independently from the external tank or, alternatively, may be only a frame, while a suitable stream of refrigerated air is created by means of an impeller fixed internally to the cover.

2 Claims, 4 Drawing Figures

APPARATUS FOR QUICK FREEZING OF AQUEOUS SOLUTIONS OR SUSPENSIONS TO BE SUBMITTED TO LYOPHILIZATION

This is a continuation of application Ser. No. 194,070, filed Oct. 29, 1971, now abandoned, which was a continuation of application Ser. No. 872,679, filed Oct. 30, 1969, also abandoned.

The present invention refers to an apparatus of new conception for quick freezing of aqueous solutions and suspensions to be submitted to lyophilization, by means of which the frozen liquid assumes such a shape on the wall of the container to allow a lyophilization in an extremely reduced time in comparison with the apparatuses used up to now.

More precisely this invention refers to a rotating freezer for the lyophilization process, particularly suitable for the treatment of a liquid contained in vials or in small containers.

It is known that the lyophilization process becomes more and more industrial importance for the preservation of products such as dehydrated ones; the so obtained dehydrated products can recover at any moment, by simple water addition, their initial chemical, physical, biochemical and bio-physical properties.

In particular the lyophilization process has reached a great importance in the pharmaceutical industry where it is used for the preservation of products such as hormones, vitamines, enzymes, antibiotics, serum, vaccines, etc. which would be altered by a prolonged contact with water, or for the preservation of medicines containing mixtures of compounds incompatible if contemporaneously present, for some time, in solution.

The lyophilization process consists essentially as it is well known in the elimination of the water contained in solid materials in aqueous solutions or suspensions, by freezing and successively sublimating said water at temperatures lower than 0°C and at absolute pressures lower than 4.57 mm Hg.

To better carry out this process, it has been found useful and often necessary, both for the freezing and the lyophilization operations to have the material under treatment distributed over surfaces as wide as possible and with thickness reduced to the minimum. While, however, with solid materials or with liquids contained in big containers (for great unitary quantities of substances) suitable techniques have been found to realize within certan limits these conditions, for liquids contained in vials or in small containers on the contrary no apparatus or process is known today which allows the liquid to freeze on wide surfaces with a minimum of thickness.

The only method presently used on industrial scale for the freezing of liquids contained in vials or small containers (hereinafter only indicated with the term of "vials" for the sake of simplicity) is the so-called "bottom" freezing method, according to which the opened vials are vertically arranged on suitable trays and these put on freezing flats of special refrigerators or (more rarely used and subjected to many inconveniences) dipped in a freezing bath. In so doing, an one-directional freezing in the first case and a bi-directional freezing in the second case is obtained, proceding in both cases from the outside towards the inside and thus freezing first the outer part of the static layer of liquid.

It is evident that these first coats of frozen liquid which have formed constitute a barrier increasingly impervious to the heat exchange with the environment, as their thickness increases. To obtain a complete freezing of the aqueous liquid contained in the vials it is thus necessary to protract the treatment for many hours. In principle for vials of a usual diametre between 13 and 14mm, with a liquid layer 10/15mm high, four hours treatment in a static freezer are required.

On the other hand, the formation of a compact pastil of frozen liquid has a determining influence also on the successive lyophilization step. As a matter of fact, the sublimation of water starts from the superficial layers then spreading in depth and consequently the vapours escaping from the pastil meet with an increasing resistance in the increasing upper layer of dried product.

In practice, for vials in the above mentioned sizes, 24 to 24 hours of drying process are necessary to reach values of residual moisture content of 0.5 up to 0.6 percent, which values are generally considered as satisfactory.

I have now realized a new freezing apparatus for liquids to be lyophilized which are contained in vials, which apparatus may be used combined with usual lyophilizers allowing a great reduction in the working time and consequently a great increase in the production with reduced costs.

The new freezer according to the invention is characterized by the fact that it essentially consists of: (a) one tank provided with refrigerated bottom and lateral walls, the top being shut by a removable air-tight cover; this tank is tiltably hinged on a support; b) one or more rotating plates or frames, for carrying trays containing the vials to be frozen which may be rotated at an adjustable speed, by means of one or more driven shafts passing through the bottom of the tank.

By suitably tilting the tank, depending on the size and the filling degree of the vials, and by rotating the movable frame generally at 10–20 revolutions per minute (but it is evident that any speed may be adopted), one can achieve the desired result of having the liquid spread on the surface of the vial and of obtaining the freezing of the liquid in thin layers of thickness adjustable according to the rotation speed and to the tilting of the axis of the tank with respect to the horizon, the liquid forming an internally concave rotation paraboloid.

Considering again as an example the case of vials of 13–14mm diameter filled with liquid up to 10–15mm height and that therefore in a static freezer would give a pastil 10–15 mm high, in the rotating freezer according to the invention, it is possible to obtain, for example, a deposit of solid frozen product having a thickness of about 2 mm on the walls of the vials of 3–4 mm maximum on the bottom.

The total freezing of such a product which, as previously mentioned, requires a minimum time of 4 hours in the static freezer, is now performed in a time which does not exceed 20 minutes, owing to the extremely great efficiency of the thermic exchange, both for the increased exchange surface and for the remarkable increase in the global coefficient of transmission of the heat.

Furthermore, the vials obtained after this new technique of freezing are dried, during the lyophilization step, in extremely reduced time as compared with those vials statically frozen. This is due to the enormous development of the evaporation surface and to the extremely reduced resistance to the vapor escape opposed by the thin coat of dried product. In practice, the 24 hours usually required for the lyophilization of the vials of the considered type, when frozen in a static freezer, are now reduced to 12 hours, thus doubling the production capacity with respect to the usual static plants and with a saving of 50 percent of the required power.

For the same reasons as above indicated it is possible to perform both the freezing and the lyophilization process at temperatures not as low as those generally used, with a consequent saving of refrigeration, which means power savings.

According to a preferred embodiment (called hereinafter A) of the rotating freezer according to the invention, a descending refrigerated stream of air which laps the whole surface of the vials to be frozen is created by means of an impeller in the inside of the cover of the tank and of an air conveyor arranged along the lateral walls of the tank and suitably spaced therefrom.

In such a case the turning plate is reduced to a frame opposing a minimum of resistance to the passage of the refrigerated air and the vial-holding trays, supported by said frame, will be suitably bored, according to the diameter of the vials, so as to allow a good circulation of the refrigerated air also on the bottom of the vials.

According to another embodiment of the present invention (called hereinafter B) in order that the thermic exchange with the liquid contained in the vials be favoured, the turning plate is itself refrigerated by means of a coil connected with the freezing means independently of the tank, thus eliminating the impeller and the air conveyor.

The construction features of the new rotating freezer according to the invention will be more clearly illustrated by the enclosed drawings where:

FIG. 4 is a plan view of the freezing tank with several frames positioned therein.

In the drawings corresponding elements are indicated with the same numbers.

Figure 1:
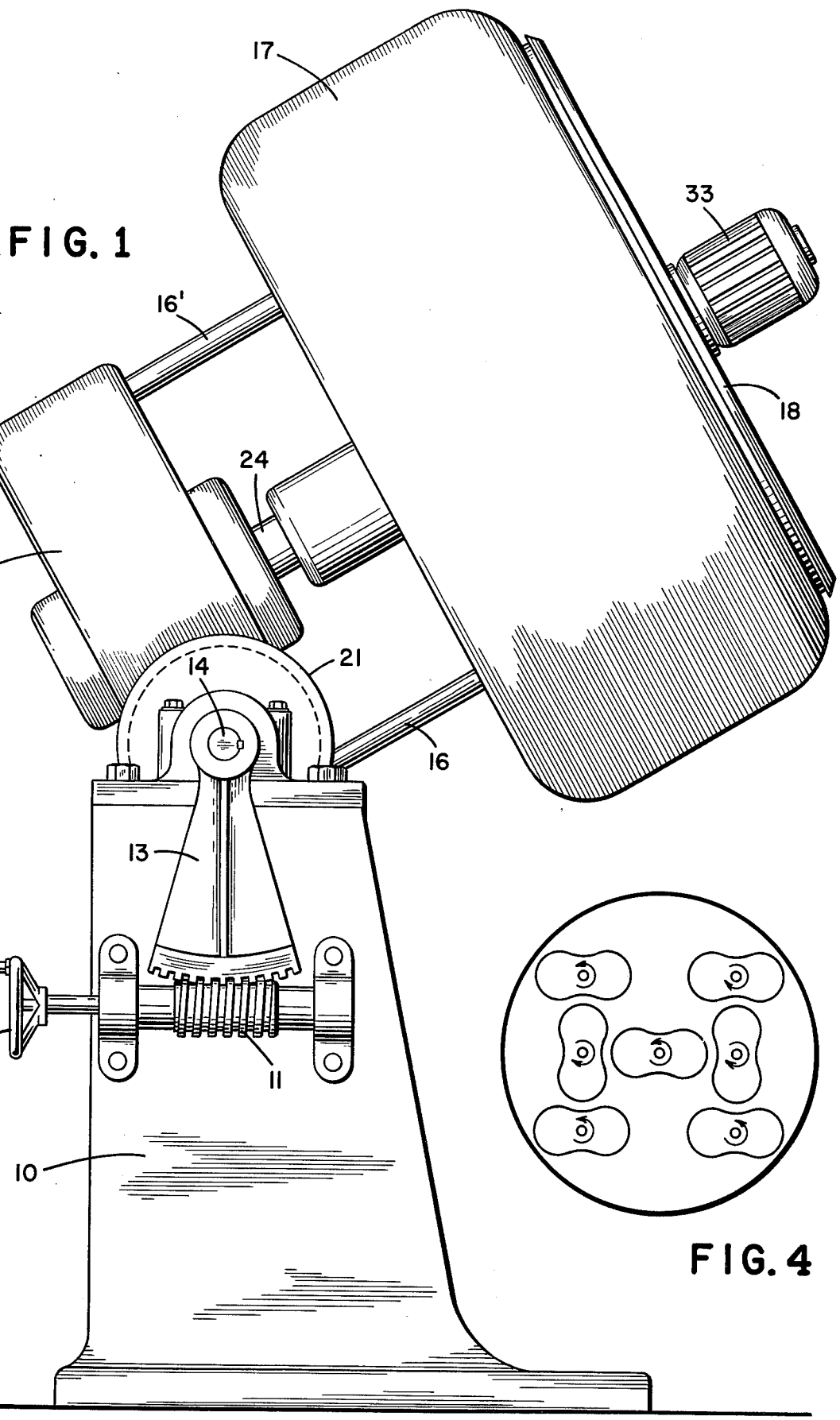
FIG. 1 is a partial side view of the freezer according to the embodiment of A.

This new freezer comprises: a pedestal 10 on which is hinged the tank through the shaft 14 keyed to the sector gear 13 engaging with the worm screw 11. This screw driven by the handwheel 12 can allow the tilting of the rotation axis of the tank between the horizontal and vertical positions. The freezer unit comprises a case 15 on which is fixed, e.g. through a plurality of trussings 16, 16', the tank 17 closed by the movable cover 18. The pedestal 10 is provided with the electric motor 19 which through the belt 20 drives the pulley 21 keyed together with a pinion or worm-screw 22 which engages with the gearwheel 23 supported, together with the shaft 24 on which the turning plate or frame 25 is fixed. The shaft 24 is mounted in case 15 through bearings 26 and 27.

The bottom and the walls of the freezing tank 17 are provided with refrigerating coils 28 connected with the input pipe 29 and the output pipe 30 of the refrigerating medium.

Figure 2:
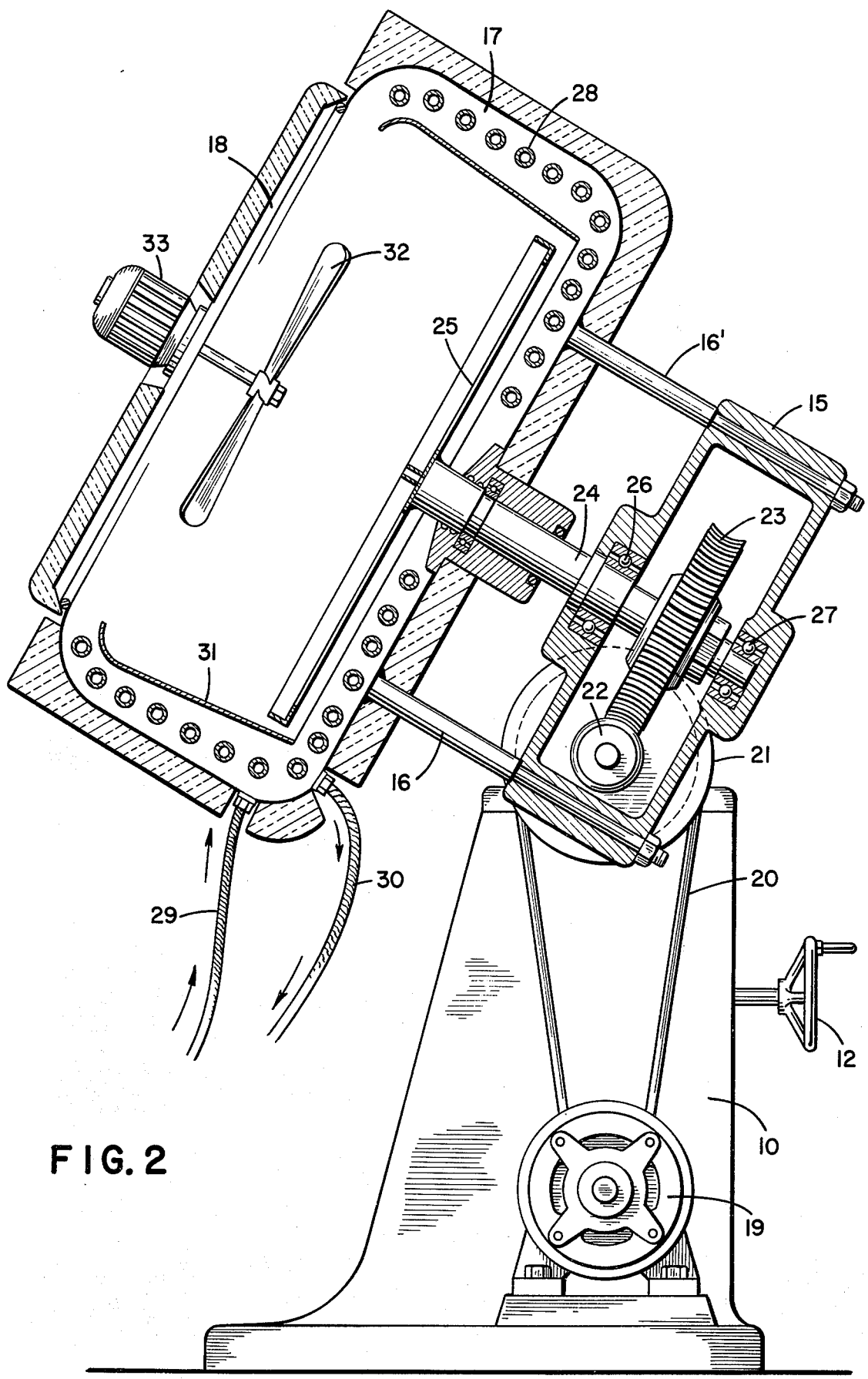
FIG. 2 is a partial vertical section, passing through the rotation axis of the vial-holding frame of the freezer of FIG. 1.

With particular reference to FIGS. 1 and 2 illustrating the embodiment A, the air conveyor 31 is shown arranged along the walls of the freezer with the impeller 32 applied inside in the center of the removable cover 18 and driven by the motor 33.

Figure 3:
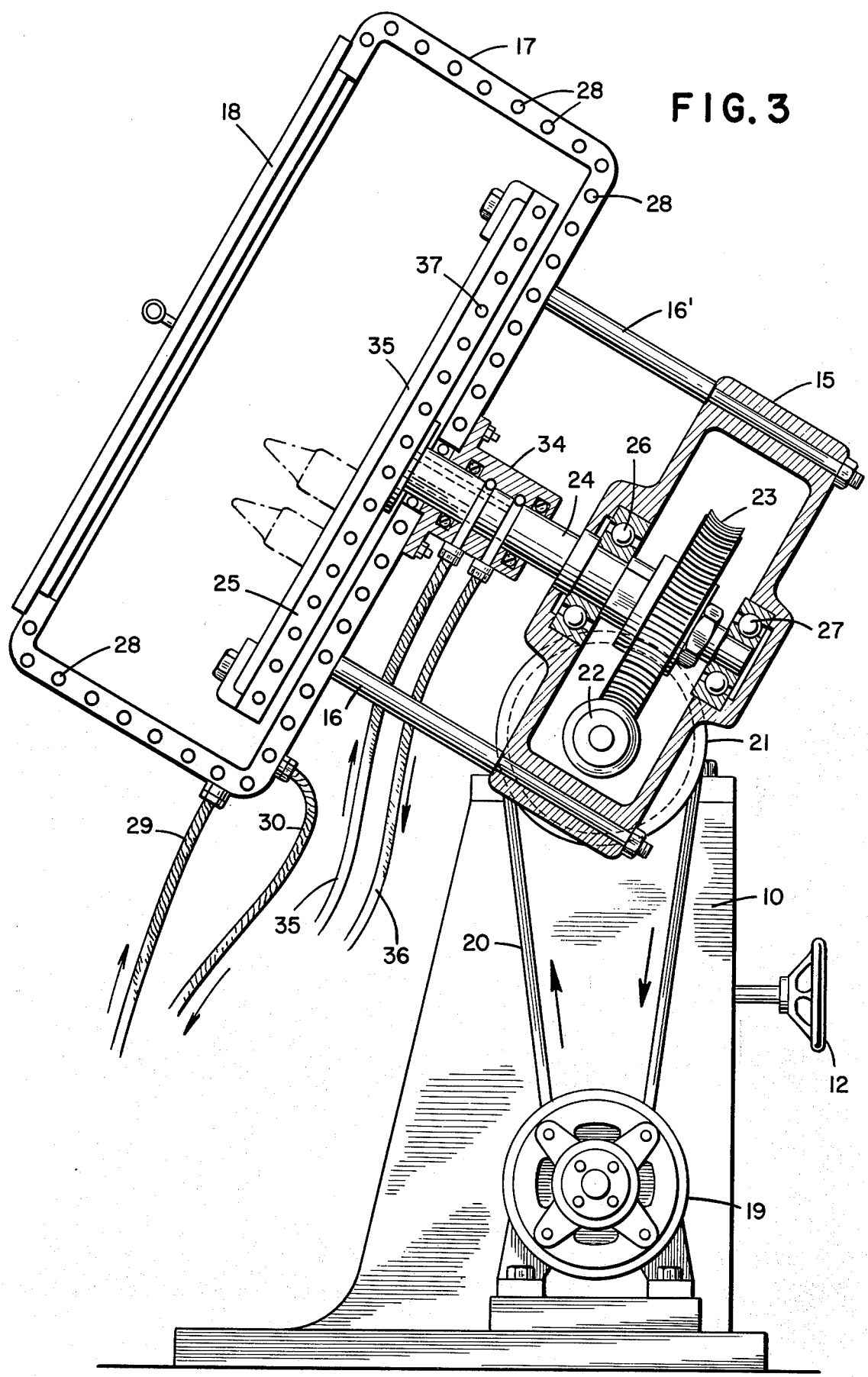
FIG. 3 is a vertical section passing through the rotation axis of the vial-holding frame of the freezer according to embodiment B.

With reference in particular to FIG. 3 illustrating the freezer according to the embodiment B, the input and output pipes 35 and 36 respectively, for the refrigerating fluid of the plate 25, enter through a suitable toroidal joint 34 in the rotating shaft 24 where suitable axial pipes are obtained which lead to the coil 37.

The new freezer may be built up in any desired size according to the production capacity required.

As previously mentioned, the new freezer may be used combined with already existing lyophilization equipment; in this case its production capacity must be adjusted to that of the existing lyophilizer to perform a simple or an integrated cycle.

If, on the contrary, one prefers to perform an integrated cycle, even the pre-existing static freezer may be used as a "storage chamber" in the working cycle, setting up a new freezer according to the invention only of very reduced dimensions and going on putting the trays filled with the frozen vials in the static freezer until the number of trays required by the lyophilizer is reached.

Supposing for instance that a lyophilization plant of the usual type, having a capacity of 24 trays is available (a type of tray commonly used is 47.8 mm long, 30.8 mm wide and 40 mm high with a capacity of 950 vials with vials having a 12–12.5 mm diameter, of 870 vials with vials having a diameter of 12.5–13 mm and 810 vials with vials having a diameter of 13.5–14 mm) it will be possible to build a rotating freezer according to the invention having a capacity of 24 trays, working discontinuously and producing each time the whole lot of vials necessary to feed the lyophilizer: alternatively it will be possible to set up a rotating freezer of a very small size having a capacity of only 2 trays and to use also the static pre-existing freezer wherein the trays produced in 12 operations of the rotating freezer are stored.

A rotating freezer of this last type (viz. 2 tray capacity) shall have a maximum diameter of 120 cm and a maximum depth of 125 cm.

In case a freezer comprising a plurality of rotating frames is wanted, it will be convenient to adopt the embodiment A and to set up a plurality of frames as illustrated in FIG. 4; this is a plan view of the freezing tank with seven frames installed.

If a motor of sufficient power is available, the frames may be so geared that by connecting to the motor only the central frame, this when moving will drive all the remaining ones. On the contrary, should the motor power be insufficient, then the frames will be averted enough to allow each to rotate independently or in pre-established groups, each driven by its own motor.

The following tables show, as an example, working times for a full lyophilization cycle carried out:

A. with lyophilization equipment of known type consisting of a static freezer of the capacity of 24 trays and of a lyophilizer also of a 24 tray capacity;

B. with the same equipment as above, comprising also the new rotating freezer according to the invention with a 2 tray capacity;

C. with an equipment comprising the new rotating freezer having a capacity of 24 trays and an ordinary lyophilizer of the same capacity.

The cycles were performed with the same vials, filled in the same manner with the same solution, since it is known that these factors have an influence on the working time. The minima working schedules (Min.) refer to compact cycles presuming to be able to eliminate any dead time, while the maxima time-schedules (Max) refer to more real cases which comprises all the unavoidable dead times peculiarly inherent to the considered type of processing.

From the above reported data it can be seen that with the integrated cycle it is possible to realize a shortening in the working time schedule (and hence a saving of energy) of 30 to 50 percent if compared to normal working time, whilst with the simple cycle one obtains, in any case, a reduction of the working time of 50 up to 55 percent; in other words one may say that this new freezer, according to the invention, allows an increase in the production capacity of a plant of 50 up to 100 percent.

It must be furthermore pointed out that, as previously indicated, both freezing and lyophilization temperatures are not as low in comparison to the traditional process, thus further reducing the energy requirement.

It is evident that although the new freezer proves particularly suitable for vials and small containers, it may be all the same properly used for bottles or solid materials by adopting some modifications, obvious to a man skilled in the art.

I claim:

1. An apparatus for quick freezing aqueous solutions or suspensions contained in vials, for subsequent lyophilization, in such a manner that said solution or suspension forms a thin frozen layer substantially on the entire inner surface of the side walls of the vials, said apparatus comprising: a tank having integral bottom and side walls and one open end, an air-tight cover for closing said open end, refrigeration means in said bottom and side walls of said tank, tank mounting means to adjustably position the longitudinal axis of the tank between horizontal and vertical positions, at least one rotatable frame mounted within said tank, means on said frame for holding trays for housing a plurality of vials, a centrally disposed rotatably driven shaft passing through the bottom of the tank and connected for driving said rotating frame, and means for refrigerating each vial from its top to its bottom including an impeller disposed centrally inside the cover, a motor disposed externally of the cover and connected for rotatably driving said impeller for producing a descending stream of refrigerated air within the central portion of said tank, air conveyor means mounted within the tank parallel to, but spaced from, said side walls defining an annular outer chamber and a coaxial cylindrical inner chamber, said impeller and air conveyor means forming a closed air circuit for said descending refrigerated stream of air in said inner chamber for lapping the entire surface of the vials from top to bottom and for a rising stream of air in said annular chamber for rapidly freezing the solution or suspension within the vials starting from the top until a thin frozen layer covers the walls of the vials.

2. An apparatus according to claim 1, in which said refrigerating means comprises refrigerating coils in the bottom and the side walls of the tank, said refrigerating coils being connected with input and output pipes penetrating through the walls of the tank.

* * * * *